United States Patent
Balasubramanian

(10) Patent No.: US 12,417,844 B2
(45) Date of Patent: Sep. 16, 2025

(54) SYSTEM AND METHOD FOR CONTACTLESS MONITORING AND EARLY PREDICTION OF A PERSON

(71) Applicant: Alpha Global IT Solutions, Harrisburg, NC (US)

(72) Inventor: Ezhilarasan Balasubramanian, Harrisburg, NC (US)

( * ) Notice: Subject to any disclaimer, the term of this patent is extended or adjusted under 35 U.S.C. 154(b) by 270 days.

(21) Appl. No.: 17/501,471

(22) Filed: Oct. 14, 2021

(65) Prior Publication Data

US 2022/0122732 A1    Apr. 21, 2022

Related U.S. Application Data

(60) Provisional application No. 63/092,997, filed on Oct. 16, 2020.

(51) Int. Cl.
| | |
|---|---|
| *G16H 50/20* | (2018.01) |
| *A61B 5/00* | (2006.01) |
| *A61B 5/11* | (2006.01) |
| *A61B 5/113* | (2006.01) |
| *G16H 20/10* | (2018.01) |

(52) U.S. Cl.
CPC ........... *G16H 50/20* (2018.01); *A61B 5/0002* (2013.01); *A61B 5/1117* (2013.01); *A61B 5/113* (2013.01); *A61B 5/4094* (2013.01); *G16H 20/10* (2018.01)

(58) Field of Classification Search
CPC ...... G16H 50/20; G16H 20/10; A61B 5/0002; A61B 5/1117; A61B 5/113; A61B 5/4094
See application file for complete search history.

(56) References Cited

U.S. PATENT DOCUMENTS

| | | | |
|---|---|---|---|
| 2019/0076098 A1* | 3/2019 | Li | G16H 10/20 |
| 2019/0336061 A1* | 11/2019 | Harrer | A61B 5/681 |
| 2020/0289033 A1* | 9/2020 | Sivertsen | A61B 5/747 |
| 2021/0169361 A1* | 6/2021 | Baker | A61B 5/4255 |
| 2021/0241912 A1* | 8/2021 | Chazin | G08B 21/0446 |
| 2022/0013238 A1* | 1/2022 | Stockwell | G16H 50/30 |
| 2022/0122735 A1* | 4/2022 | Sherkat | G06N 3/04 |

(Continued)

*Primary Examiner* — Sheetal R Paulson
(74) *Attorney, Agent, or Firm* — Lambert Shortell & Connaughton; David J. Connaughton, Jr.; Justin P. Tinger

(57) ABSTRACT

Disclosed is a contactless event monitoring and early detection method and system of real time monitoring of a person to predict an undesired event. The contactless event monitoring and early detection method collects data from a one or more data aggregation devices and filters the collected data in a signal processor. The contactless event monitoring and early detection method then analyzes the collected data in an event monitoring and detection processor. The event monitoring and detection processor implementing artificial intelligence algorithms to predict the probability of the occurrence of to the undesired event. Further, the event monitoring and detection processor receives a health data related to the person and selects an analytical model to be applied for prediction of the undesired event. In one embodiment, the probability of occurrence of the undesired event is associated on a threshold value. The threshold value is related to at least one early indicator associated with the person. The contactless event monitoring and early detection method then preempts the person about the onset of the undesired event by sending an alert to the person and a caretaker for remedial action.

20 Claims, 8 Drawing Sheets

(56) References Cited

U.S. PATENT DOCUMENTS

| | | | |
|---|---|---|---|
| 2022/0265219 A1* | 8/2022 | An | G16H 50/30 |
| 2023/0238142 A1* | 7/2023 | Zotelo | G16H 20/00 705/3 |

* cited by examiner

SYSTEM AND METHOD FOR CONTACTLESS MONITORING AND EARLY PREDICTION OF A PERSON

CROSS-REFERENCE TO RELATED APPLICATIONS

This application claims the benefit of U.S. Provisional Patent Application No. 63/092,997 filed on Oct. 16, 2020 which is herein incorporated by reference in its entirety.

FIELD OF THE INVENTION

The present invention is related to a method and system of contactless monitoring and assessment of a person without any privacy intrusion. More specifically, the invention provides a real time monitoring and early detection of an undesired event associated with a person.

BACKGROUND OF THE INVENTION

Continuous monitoring of a person is required for different reasons specifically for sick or ill people. Other persons may require continuous monitoring due to old age, diseases, medical care after a surgery or other reasons. All these people due to some reason or the other or due to their medical state need contactless monitoring. In addition, these people may not be comfortable with caretakers visiting them frequently to check different medical parameters. In addition, devoting one caretaker per person may be highly expensive and impractical due to lack of resources and manpower. Also, the contactless monitoring and early detection may also be required under other circumstances such as outbreak of pandemic and/or monitoring people at public places. Due to the non-intrusive nature of the solution, this can be used even in private areas like restrooms. In several situations, continuous monitoring of the person/person(s) is performed to avoid undesired events. An added advantage of continuous monitoring is that the caretakers can take remedial actions in case of emergencies. Furthermore, it preempts the caretaker to take necessary action in order to avoid an undesired event/situation. Likewise, several other reasons such as risk of infection after surgery, a person suffering from an infectious disease, isolation due to insanity or other reasons the person may be kept in an isolated environment and can be monitored in a contactless manner. However, such persons also need continuous monitoring so that any emergency can be attended immediately. All these scenarios and use cases point to a need for a method and system for continuous monitoring that can alert the caretaker in case of emergency or can even take remedial action on its own.

A method and system is required that can monitor a person or a subject in a contactless manner. The contactless monitoring and early detection system disclosed herein provide a solution to the problems disclosed above. The contactless monitoring system can fulfill all the requirements of remote monitoring, that is, alert the person/subject of an undesired event, alert the caretaker of the undesired event, raise an alarm in case of emergency The present invention provides a novel method and system of contactless assessment of a person based on aggregated data collected from different data points. More specifically, the invention provides forecasting an occurrence of an event based on real time collection of data characteristics aggregated from different data collection points.

SUMMARY

Disclosed is a contactless event monitoring and early detection method for real time monitoring of a person to predict an undesired event, the contactless event monitoring and early detection method comprising: collecting data from a one or more data aggregation devices; filtering the collected data in a signal processor; analyzing the collected data in an event monitoring and detection processor, the event monitoring and detection processor implementing artificial intelligence algorithms to predict the probability of the occurrence of to the undesired event; receiving a health data related to the person; selecting an analytical model to be applied for prediction of the undesired event, wherein the probability of occurrence of the undesired event associated on a threshold value and wherein the threshold value is related to at least one of early indicator associated with the person, and preempting the person associated with the undesired event by sending an alert to the person and a caretaker for remedial action.

Disclosed is a contactless event monitoring and early detection system for real time monitoring of a person to predict an undesired event, the contactless event monitoring and early detection system comprising: one or more data aggregation devices for collecting data; a signal processor for filtering and removing the unwanted frequencies from the collected data; a database for storing the aggregated data and to receive a health data associated with the person; an artificial intelligence module comprising deep learning algorithms and a rule based engine for building an analytical model to predict the undesired event based on the collected data and a threshold value, and wherein the threshold value is at least based on the health data of the person; an analytical database for storing one or more analytical models; a prediction module implementing at least one of the analytical model to predict the occurrence of the undesired event to forewarn the person and a caretaker by sending a notification or alert to take a remedial action.

In embodiments, the undesired event is associated with detection of a fall, a seizure, an abnormal breathing of a person. The fall of a person can be a person falling from a sitting position, falling from a bed or fainting on to the ground from a chair or on a bed. The seizure of a person may be related to stressed up muscles, brain stroke, inability of a person to make a desired movement or unable to perform a routine job due to medical condition. Likewise abnormal breathing may be related to high rate or lower rate of breathing than the normal breathing rate of 12 to 16 per minute.

In embodiments, the remedial action to halt the occurrence of the undesired event is related to taking a preventive medicine. The preventive medicine may be related to a lifesaving drug, a prescribed medicine by a doctor or a medicine for controlling a worsening condition of a person.

In embodiments, the threshold value may be related to early indicators before the onset of the undesired event. For example, the early indicators may be pain in arm or breathless, increase in blood pressure and/or pulse rate. These may be early indicators for a heart attack.

In embodiments, the health data includes at least one of a personal data, a disease history, a medication data or genetic data of a person. The personal data may include age, name, sex, social security number and other personal data. The disease history may include information related to chronic, non-chronic disease or other hereditary diseases. The medication data includes the data related to prescribed and other medicine taken by the person. The genetic data may include gene data providing information related diseases that might affect the person.

In some embodiments, probability of the undesired event is determined by comparing the predicted value with a threshold value. In embodiments, the threshold value related to the undesired event is associated with the health data of a person. For example, the threshold value of a person with heart disease as shown in the health data will be less than the person that doesn't have any heart disease in the health data. In some embodiments, the threshold value related to the person is automatically set by the artificial intelligence algorithms based on the training data set and the health data of the person, past history related to undesired event and the personal data such as age, sex and the like.

In embodiments, the one or more data aggregation devices include at least a one or more sensors, a one or more RFID devices and a one or more thermal cameras or some other devices.

In some embodiments, the analytical models are developed using one or more training data sets and stored in the analytical database and frequently updated based on new training data that has been aggregated from both internal and external sources.

A method of correcting an error in prediction of an undesired event associated with a person during real time monitoring, the contactless event monitoring and early detection method comprising step of: collecting data from a one or more data aggregation devices; filtering the collected data in a signal processor; analyzing the collected data in an event monitoring and detection processor, the event monitoring and detection processor implementing artificial intelligence algorithms to predict the probability of the occurrence of to the undesired event; receiving a health data related to the person; selecting an analytical model to be applied for prediction of the undesired event, wherein the probability of occurrence of the undesired event associated on a threshold value and wherein the threshold value is related to at least one of early indicator associated with the person; receiving an input from the person or a caretaker that the prediction of the undesired event was false; retraining the artificial intelligence algorithms to correct the false prediction of the undesired event to updated at least one analytical model, and storing the updated analytical model in the database and using the updated analytical model for predicting and undesired events.

In embodiments, the error associated with the undesired event may be a false positive or false negative.

Disclosed is the system and method of a contactless event monitoring and early detection method for real time monitoring of a person to correct an occurrence of a false undesired event, the contactless event monitoring and early detection comprising: collecting data from a one or more data aggregation devices; filtering the collected data in a signal processor; analyzing the collected data in an event monitoring and detection processor using deep artificial intelligence algorithms to associate the data with the undesired event; associating the probability to predict the occurrence of to the undesired event; receiving other data related to the person comprising at least the health data; selecting an analytical model to be applied for prediction of the undesired event, wherein the probability of occurrence of the undesired event is based on threshold value; receiving the an input from the person or a caretaker that the prediction of the undesired event was false; retraining the analytical models using the new data related to false prediction of the undesired event and recreate an updated analytical models, and storing the updated analytical models in the database for predicting of the occurrence of the undesired event.

In embodiments, the false occurrence of the undesired event is false negative. A false negative is the state that an undesired event never occurred but the contactless event monitoring and early detection capture it. In some embodiments, the contactless event monitoring and early detection system may include self-healing capabilities to capture a false negative and to automatically correct it.

Disclosed is a method of correcting the failure of capturing an undesired event during real time monitoring of a person, the contactless event monitoring and early detection method comprising step of: collecting data from a one or more data aggregation devices; filtering the collected data in a signal processor; analyzing the collected data in an event monitoring and detection processor using deep artificial intelligence algorithms to associate the data with the undesired event; associating the probability to predict the occurrence of to the undesired event; receiving other data related to the person comprising at least the health data; selecting an analytical model to be applied for prediction of the undesired event, wherein the probability of occurrence of the undesired event is based on threshold value; receiving an input from the person or a caretaker that the prediction of the undesired event went unnoticed; retraining the artificial intelligence algorithms to account for failed prediction of the undesired event and recreating an updated analytical model, and storing the updated analytical model in the database and using the updated analytical model for predicting and undesired events.

In embodiments, the method of correcting the failure of an undesired event is related to a false positive or a false negative. A false positive is the state that the contactless event monitoring and early detection sends an alert when no such event occurred. A false negative is the state that an undesired event occurred but the contactless event monitoring and early detection failed to capture it. In some embodiments, the contactless event monitoring and early detection system may include self-healing capabilities to capture a false positive and false negative, and automatically correcting it.

Disclosed are methods and systems for event monitoring, early warning and contactless detection. The event monitoring and early detection system analyses the data aggregated from multiple data sources for a person or a subject to forecast a probability of an undesired event. The event monitoring and early detection system or the contactless detection, early prediction and alert method and system comprises: a one or more sensors for aggregating data from an environment and one or more person; filtering the aggregated data using one or more data filtration techniques; passing the filtered data to a central processor, wherein the central processor comprises an analytical database implementing analytical models for analyzing the filtered data; and applying at least one data model to analyze the filtered data to predict a one or more undesired events related to a person.

The contactless detection, early detection, early prediction and alert method and system comprises an event monitoring and detection module configured to receive: aggregating data from a one or more sensors and for one or more person; filtering the aggregated data using one or more data filtration techniques; passing the filtered data to an event monitoring and detection system comprising an analytical database implementing analytical models for analyzing the filtered data; and applying at least one data model to analyze the filtered data to predict a one or more desired or undesired events related to a person.

In embodiments, the contactless detection, early detection, early prediction and alert method and system may be a homecare monitoring system for a patient, an old age home for monitoring old persons, a care Centre for humans with special needs, a recovery Centre for persons suffering for specific medical condition requiring continuous monitoring. In embodiments, the medical condition may include but not limited to autism, cancer, heart stroke, accident, coma, brain damage or some other type of medical condition.

In other embodiments, the contactless detection, early detection, early prediction and alert method and system may be implemented in airports, in public places such as malls, shopping complexes, rail stations, bus stations, banks and other public places requiring monitoring and detection.

In embodiments, the person suffering from a medical condition may be an adult, a child, an old person, a mentally retarded person, a physically challenged person or a person having a medical condition from birth that required continuous monitoring of his/her physical activity.

In embodiments, sensors may be a Radio Frequency (RF) sensor, a vision and imaging sensor, a temperature sensor, a radiation sensor, a proximity sensor, a pressure sensor, a position sensor, a photoelectric sensor, a particle sensor, a motion sensor, a metal sensor, a level sensor, an electrical sensor, a contact sensor, a non-contact sensor or any combination of sensors.

In some embodiments, the sensor may include a microcontroller having inbuilt capability to process and filter signals. In embodiments, the sensor having a microcontroller with inbuilt capability to process and filter signals may be tuned at a specific frequency.

In some other embodiments, the sensor having a microcontroller with inbuilt capability to process and filter signals may be a band pass filter tuned to pass a particular set of frequencies while attenuating all other frequencies.

In yet another embodiment, the sensor having a microcontroller with inbuilt capability to process and filter signals may include one or more band pass filters.

In embodiments, the undesired event may be related to a fall of a person, seizure of one or more body parts of a person, abnormal breathing of a person, inactivity of a person during consciousness, heart stroke, a brain stroke or some other type of medical that requires immediate attention. The prediction of a fall and/or seizure based on a person is at least based on a normal behavior and/or on one or more indicators, which are aggregated by data aggregation points over different periods of time.

In embodiments, event monitoring and detection method and system or the contactless detection, early prediction and alert method and system may predict early intervention during any breathing abnormalities during sleep.

In some embodiments, the contactless event monitoring and early detection system may be configured to perform contactless detection, early prediction and alerts/notifications. In embodiments, the contactless monitoring system may monitor and provide alert and notification to different stakeholders such as but not limited to a person, a stakeholder, a hospital, a personal physician, a nurse or some other health worker associated with the person.

In some embodiments, contactless early prediction method and system may perform in the background prediction of undesired events and provide intervention in handling the undesired event over a specified time or on occurrence of specific medical event such as but not limited to fever, fall, sleep, unconsciousness and other medical states.

In embodiments, contactless event monitoring and early detection method and system may ensure that there is no private data accessed during monitoring including the accesses to any private areas such as but not limited to a bathroom, a bedroom and other private areas.

In embodiments, the aggregated data from different sources and directions (specific to directional sensors) process the collected data at a central unit, estimates and forecasts an occurrence of the undesired event, and sends notification/notifications for taking necessary action to stop the occurrence of the undesired event.

BRIEF DESCRIPTION OF THE DRAWINGS

Different embodiments will now be described in detail with reference to the drawings, in which.

DETAILED DESCRIPTION OF THE INVENTION

The examples are not intended to be limiting. The different illustrations in block diagrams are not limiting and can be combined, omitted or organized with other components or organized into different architectures. Reference will now be made in detail to specific implementations of the present invention as illustrated in the accompanying drawings. The same reference numbers will be used throughout the drawings and the following description to refer to the same or like parts.

The term "undesired event" refers to a medical state such as but not limited to stroke, heart attack, autism, fall, seizure and abnormal breathing. An undesired event can also be any medical state that requires immediate attention of a doctor, a caretaker, or a patient. Additionally, any life-threatening medical condition can also be an undesired event.

The term "early indicators" refer to symptoms associated with undesired events that are visible of an onset of the disease or medical condition in the early stage of the disease.

Figure 1A:
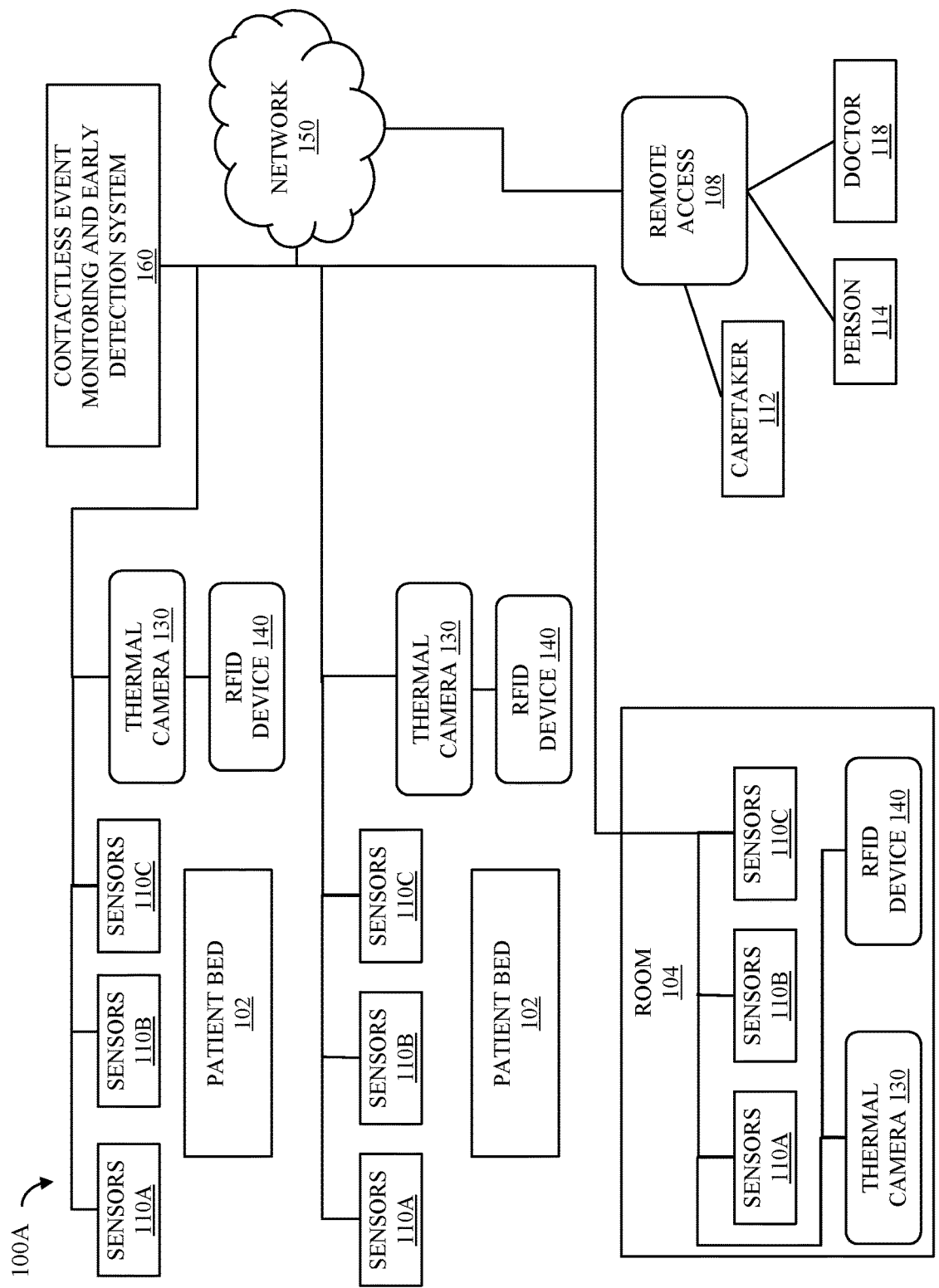
FIG. 1A illustrates of the operating environment of a contactless event monitoring and detection system in an embodiment of the present invention.

FIG. 1A illustrated the operating environment of a contactless event monitoring and early detection system in an embodiment of the present invention. The operating environment 100A comprises one or more data aggregation devices, which include a sensor 110A, a sensor 110B and a sensor 110C (collectively referred as sensors 110), a one or more thermal camera 130, a one or more RFID device 140, a one or more patient beds 102 for monitoring persons, a one or more rooms 104, a contactless event monitoring and early detection system 160, a remote access 108, which is configured to transmit undesired events and/or remedial actions to a caretaker 112, a person 114, and a doctor 118.

The one or more data aggregation devices such as sensors 110, the one or more thermal camera 130, and the one or more RFID devices 140 are connected to the contactless event monitoring and early detection system 160 directly or through a wired network or a wireless network. The one or more data aggregation devices are the part of the contactless event monitoring and early detection system 160 may monitor one or more patient beds 102 or one or more rooms 104 remotely. The one or more patient beds 102 and one or more rooms are occupied by persons 114 to be monitored. The contactless event monitoring and detection system 160 may collect and process the aggregated data from one or more data aggregation devices for one or more persons 114 to capture undesired events related to each person 114. The undesired events and remedial action may be passed for each person 114 over the network 150 to the remote access device 108. The remote access device 108 transmits the information over to different devices, which are provided to the person 114, the caretaker 112, and the doctor 118. In embodiments, the contactless event monitoring and early detection system 160 may be implemented on a cloud computing environment, a client server environment, a distributed networked environment or some other type of computing environment.

In different embodiments, the remote access device 108 may be a Wi-Fi router, a wireless access point, a wireless transmitter/receiver or some other wireless communication device.

In embodiments, the person 114 may be a patient, a mentally sick person, a differently abled person or a person suffering from autism. Alternatively, the person 114 may be any individual suffering from a chronic or a non-chronic disease. Alternatively, the contactless event monitoring and early detection system 160 may be implemented in hospitals, malls, airports to monitor one or more persons 114.

In embodiments, the data aggregation devices may also include but not limited to different types of sensors 110, one or more thermal cameras 130, one or more RFID devices 140 and medical equipment, RGB cameras, smart devices installed at home or some other type of devices.

Figure 1B:
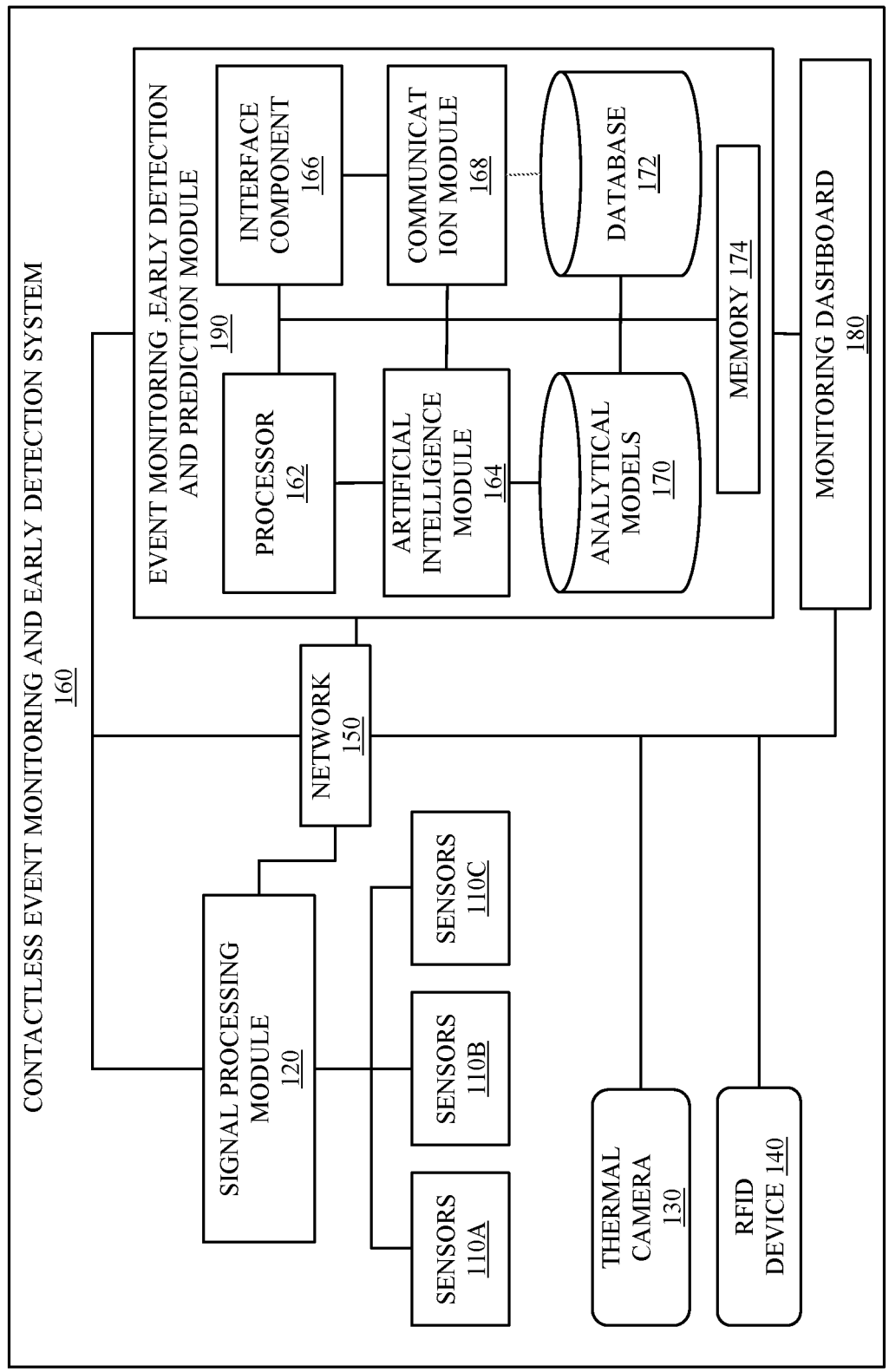
FIG. 1B illustrates different modules of the contactless event monitoring and detection system in an embodiment of the present invention.

FIG. 1B illustrates different modules of a contactless event monitoring and early detection system in an embodiment of the present invention. The contactless event monitoring and detection system 160 includes sensors 110, one or more thermal cameras 130, and one or more RFID devices 140, a monitoring dashboard 180, and an event monitoring, early detection and prediction module 190 apart from other modules.

The sensors 110 may be configured and connected to a signal processing module 120, which filters, amplifies and conditions the radio waves signal received from one or more sensors 110. In some embodiments, the data aggregation devices may also include an X-ray, a CT scanner, a remote blood pressure monitoring equipment, an oxygen concentrator and other medical equipment that can be used by the person 114 for self-help on receiving an alert. The one or more thermal cameras 130, the one or more RFID devices 140 and the signal processing module 120 are configured to the network 150. In addition, the network 150 is connected to the monitoring dashboard 180 and the event monitoring, early detection and prediction module 190.

In different embodiments, the network 150 may either be a wired network or a wireless network. The contactless event monitoring and early detection system 160 may implement one or more wireless protocols for communicating with the network 150 such as but not limited to 802.11, Edge, Bluetooth, NFC, Wi-Fi or some other wireless protocols.

The RFID devices 140 may provide additional information about the environment and alert the person 114 of nearby surrounding environments to avoid collision with nearby objects. For example, the RFID devices 140 may be scattered along with the sensors 110 to provide an accurate dimension of the surrounding environment. In some embodiments, at least one of the RFID devices 140 may be worn by the person 114 or may be attached to clothes in the form of buttons or collar or shoes; the person 114 may be provided with notifications or alerts about the different objects in vicinity. In this way the person 114 may get accurate information regarding his coordinates and surrounding to avoid fall or collision with nearby objects. Likewise, the thermal camera 130 camera provides accurate location information about the object during night by combining the aggregated data from the sensors 110, the RFID devices 140, and the thermal camera 130.

The one or more thermal cameras 130 are optional, but in some embodiments, the thermal cameras 130 may be employed along with the sensors 110 to accurately measure the body temperature. Although only one thermal camera 130 is shown in alternative embodiments more than one thermal camera 130 may be attached. The thermal camera 130 may be particularly useful when the contactless event monitoring and early detection system 160 is configured to accurately map the space for movement of the person 114 in a dark room. For example, to help in navigation of the person, who is partially blind.

The signal processing module 120 connected with one or more sensors 110 filters the electrical signal to remove unwanted noise. In some embodiments, the signal processing module 120 may apart from filtering the electrical signal may also amplify the weak signal from the one or more sensors 110. Additionally, the signal processing module 120 may filter electrical signals to discard unwanted frequencies bands and pass band frequencies associated with each of the sensors 110.

In some embodiments, the analog signal may be converted into digital signal to reduce noise in the electrical signal. In other embodiments, the signal may be conditioned, which may include filtration and amplification of electrical signals received from one or more sensors 110. In some embodiments, the signal processing module 120 may process and filter both analog and digital signals.

The event monitoring, early detection and prediction module 190 includes a processor 162, an artificial intelligence module 164, an interface component 166, a communication module 168, an analytical model 170 and a database 172 and a memory 174.

In embodiments, the processor 162 may be a microcontroller, a microprocessor, an embedded processor, a Digital Signal Processor (DSP) and/or a media processor. Furthermore, the processor 162 may be a high-end processor, single, dual or multiple core processor, multi-threaded processor, turbo boost enabled processor, hyper-threading enabled processor or some other type of processor.

The interface component 166 may include an I/O controller 314, an interface bus, a data transfer bus, a power supply cable or some other type of interface component. The interface bus may provide data transfer among different modules apart from providing electrical power to different modules.

A communication module 168 enables transfer of data between the sensors 110, the signal processing module 120, the thermal camera 130, the RFID device 140, the monitoring dashboard 180 and the event monitoring, early detection and prediction module 190.

The memory 174 may be a ROM, RAM or some other type of memory.

The artificial intelligence module 164 includes deep learning algorithms, which are applied to the data received from the sensors 110, the thermal camera 130 or the RFID device 140. Analytical models 170 are stored in a database. In one embodiment, the analytical models 170 includes an analytical database, which stores analytical model(s) for prediction of an undesired condition such as but not limited to fall prediction, seizure prediction, and abnormal breathing. In some embodiments, the analytical model 170 includes an analytical database and may also store health data of the person 114.

In some embodiments, the analytical models 170 may be utilized for predicting a desired event. For example, the analytical models may be applied to determine when a person is likely to have normal breathing after a medication. However, in preferred embodiments, the analytical models are implemented to capture the undesired event. The artificial intelligence module 164 may update the analytical models 170 in real time at different time periods in order to make accurate predictions of the undesired events.

The database 172 stores data related to person location history, the navigation history, and other information related to movement. In addition, the database 172 may store health information and/or health data, which includes personal information, genetic information, vaccination information, drug allergy information, hospitalization information, medication information, diseases associated with the person 114 such as but not limited to chronic and non-chronic diseases. The database 172 may regularly update the health information of the person 114 in real time to ensure accurate prediction of the undesired events. The artificial intelligence module 164 may then utilize the health information of each person 114 to arrive at a threshold value to predict the undesired event. The personal information may include parameters related to the person 114 such as but not limited to age, sex, profession, special needs, diseases, treatment protocols and medicines, account, identification details, emergency contact and other parameters related to the person.

The database 172 provides the health information to the artificial intelligence module 164, which selects at least one analytical model 170 to predict the undesired events associated with the person 114 and pass the information to the person 114, the caretaker 112, and the doctor 118. Based on the type of undesired event associated with the person 114, the event monitoring, early detection and prediction system 190 may provide remedial action associated with the undesired event.

In another embodiment, the database 172 provides health information of the person 114 to the artificial intelligence module 164. The artificial intelligence module 164 then implements at least one analytical model based on a predefined criteria to arrive at a threshold value. The threshold value is passed and stored in the database under profile information of each person 114. The threshold value is different for different persons and is utilized to trigger an undesired event if the predicted value calculated by analytical models 170 is higher or equal to the threshold value.

In yet another variation of this implementation, the artificial intelligence module 164 may receive information related to a person, which may include personal data, medical history, physical condition and other related data. This aggregated data is stored in a database 172. The artificial intelligence module 164 may validate the accuracy of the analytical models 170 and if required retain the analytical models 170 to arrive at an updated threshold value.

In yet another embodiment, the database 172 provides the health information and the location information to the artificial intelligence module 164, which select at least one analytical model 170 to predict the undesired events associated with the person 114 and pass the information to the person 114, the caretaker 112, and the doctor 118. Based on the type of undesired event associated with the person 114, the event monitoring, early detection and prediction module 190 may provide remedial action associated with the undesired event. For example, if the location of person 114 is the bathroom then artificial intelligence module 164 may use a different analytical model 170 for prediction of the undesired event associated with person 114.

In embodiments, the event monitoring, early detection and prediction module 190 may predict the undesired event associated with different persons in parallel using parallel processing.

In embodiments, the database 172 may be a relational database or a SQL database such as MySQL, NoSQL databases such as MongoHQ, Graph DB, key-value stores and file system storage such as a syslog buffer.

In embodiments, the database 172 may reside on a server, a cloud, or distributed environment and may be implemented as a distributed database, a standalone database, or as a client server database. In this case, the database 172 is configured to the event monitoring, early detection and prediction module 190 through a wired or wireless network.

In different embodiments, the artificial intelligence module 164 may implement different deep learning algorithms such as but not limited nearest neighbor, k-nearest neighbors, support vector machines, naive Bayesian, decision trees, random forests, logistic regression, and/or linear discriminant analysis. In some embodiments, the machine learning module may implement artificial neural networks, deep learning, support vector machines and other deep learning algorithms.

In some embodiments, the artificial intelligence module 164 may implement analytical models 170 for fall detection. The analytical models 170 for fall detection may depend on one or more parameters related to the person 114. The one or more parameters may be extracted from the profile of the person 114 stored in the database 172. For example, if the artificial intelligence module 164 accesses the personal data and find that the person 114 is old and weak then it will select a different analytical model 170 compared to the analytical model, which is selected and applied in case of a young person with a disability.

In embodiments, the contactless event monitoring and early detection system 160 may include a feedback module to handle false alerts, for example, a false positive alert happens when the contactless event monitoring and early detection system 160 triggers an undesired event and passes it to the person 114 and the caretaker 112. The caretaker 112 and/or the person 114 provide feedback that no undesired event has happened and the alert was a false alert due to some reason. Likewise, a false negative may happen when the contactless event monitoring and early detection system 160 fails to capture an undesired event and no alert related to the undesired event is provided to the person 114 or the caretaker 112. In such cases, the artificial intelligence module 164 may record the false positive and false negative in the database 172 and accordingly update the analytical models 170 to address the false alerts.

The contactless event monitoring and early detection system 160 is connected to the monitoring dashboard 180. The monitoring dashboard 180 may display information to one or more stakeholders related to monitoring and undesired events such as but not limited to the caretaker 112, the person 114 and the doctor 118. In one embodiment, the monitoring dashboard 180 may display information to one or more stakeholders related to monitoring and desired events.

The monitoring dashboard 180 may also receive information directly from the signal processing module 120, the one or more thermal cameras 130 and the one or more RFID devices 140 through the network 150. The monitoring dashboard 180 may display different parameters related to a particular person to the caretaker 112. In addition, monitoring dashboard 180 may provide alerts and notification in text and graphics form to the caretaker 112 related to the undesired events associated with the person 114.

Figure 2:
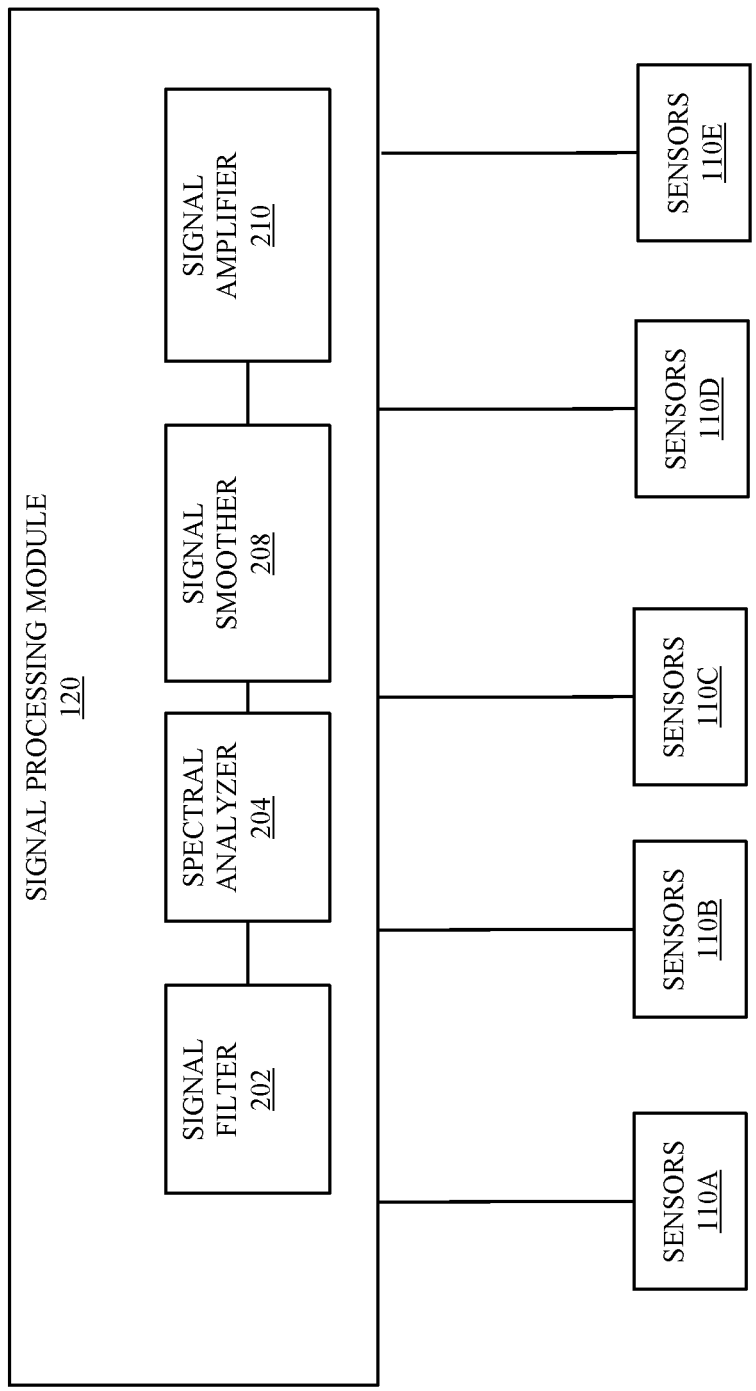
FIG. 2 illustrates different components of a signal processing module in an embodiment of the present invention.

FIG. 2 illustrates different components of a signal processing module in an embodiment of the present invention. The signal processing module 120 includes a signal filter 202, a spectral analyzer 204, a signal smoother 208, and a signal amplifier 210 apart from other modules. The signal filter 202 receives the radio frequency signal from one or more sensors 110 (for example, sensor 110A, sensor 110B, sensor 110C, sensor 110D, and the sensor 110E). Although only five sensors 110 are shown in FIG. 2, however, in other embodiments, the number of sensors 110 may vary based on different parameters such as but not limited to blind spots coverage, person's monitoring needs, location, size of the room, number of persons, room architecture.

The signal filter 202 may remove unwanted noise from the radio frequency signal received from one or more sensors 110. In addition, the signal filter 202 may improve signal immunity, signal-to-noise ratio, filter out unwanted frequency, and separate single frequency from a spectrum of frequencies, which are required for prediction of undesired events.

In embodiments, the signal filter 202 may be a combination of one or more filters. Further, the signal filter 202 may either be a passive filter or an active filter.

The output of the signal filter 202 is connected to the spectral analyzer 204. In some embodiments, the spectral analyzer 202 may be bypassed. The spectral analyzer 204 may receive the filtered signal from the signal filter 202 and perform a real time spectral analysis. The spectral analyzer 204 converts the received signal from the one or more sensors 110 from time domain into frequency domain. The main function of the spectral analyzer 202 is to ensure that all frequencies that contribute to the prediction of any undesired events and/or anticipated events are considered and amplified for further processing. In some embodiments, a large number of sensors are deployed, in this type of deployment there is always a likelihood of a frequency overlap. To address the problem of frequency overlap and frequency separation, the frequency domain analysis of signals using Fast Fourier Transform may provide an optimized frequency separation for different signals.

In some embodiments, the Fast Fourier Transform is performed separately on the signals received from each of the sensors 110, such as sensor 110A. This allows separation of signals in the frequency domain so that each signal is analyzed for undesired events by the event monitoring, early detection and prediction module 190.

The output of the spectral analyzer 204 is passed to the signal smoother 208. The signal smoother 208 reduces abrupt changes in signals received from sensors 110 to demarcate signal outliners. In one embodiment, the signal outliers identified by the signal smoother 208 are analyzed separately by the event monitoring, early detection and prediction module 190 to ensure that the signal outliners, which are discarded, do not provide additional information for prediction of the undesired events and/or anticipated events.

The signal smoother 210 reduces the time-amplitude values and/or time-frequency values to a minimum set of values without losing any signal information and reduces bandwidth in a wireless transmission.

In some embodiments, the signal processing module 120 may be directly connected to the monitoring dashboard 180 to display some parameters that are lifesaving or that don't require immediate action in the event monitoring, early detection and prediction module 190 fails to capture an undesired event, which is life threatening.

In some embodiments, the time-frequency values may be multiplexed from different sensors 110 and passed to the event monitoring, early detection and prediction module 190. In some other embodiments, the time-amplitude values may be multiplexed from different sensors 110 and passed to the early detection and alert/event monitoring and detection system 160. In yet some other embodiments, the time-amplitude-frequency values may be multiplexed from different sensors 110 and passed to the event monitoring, early detection and prediction module 190.

Figure 3:
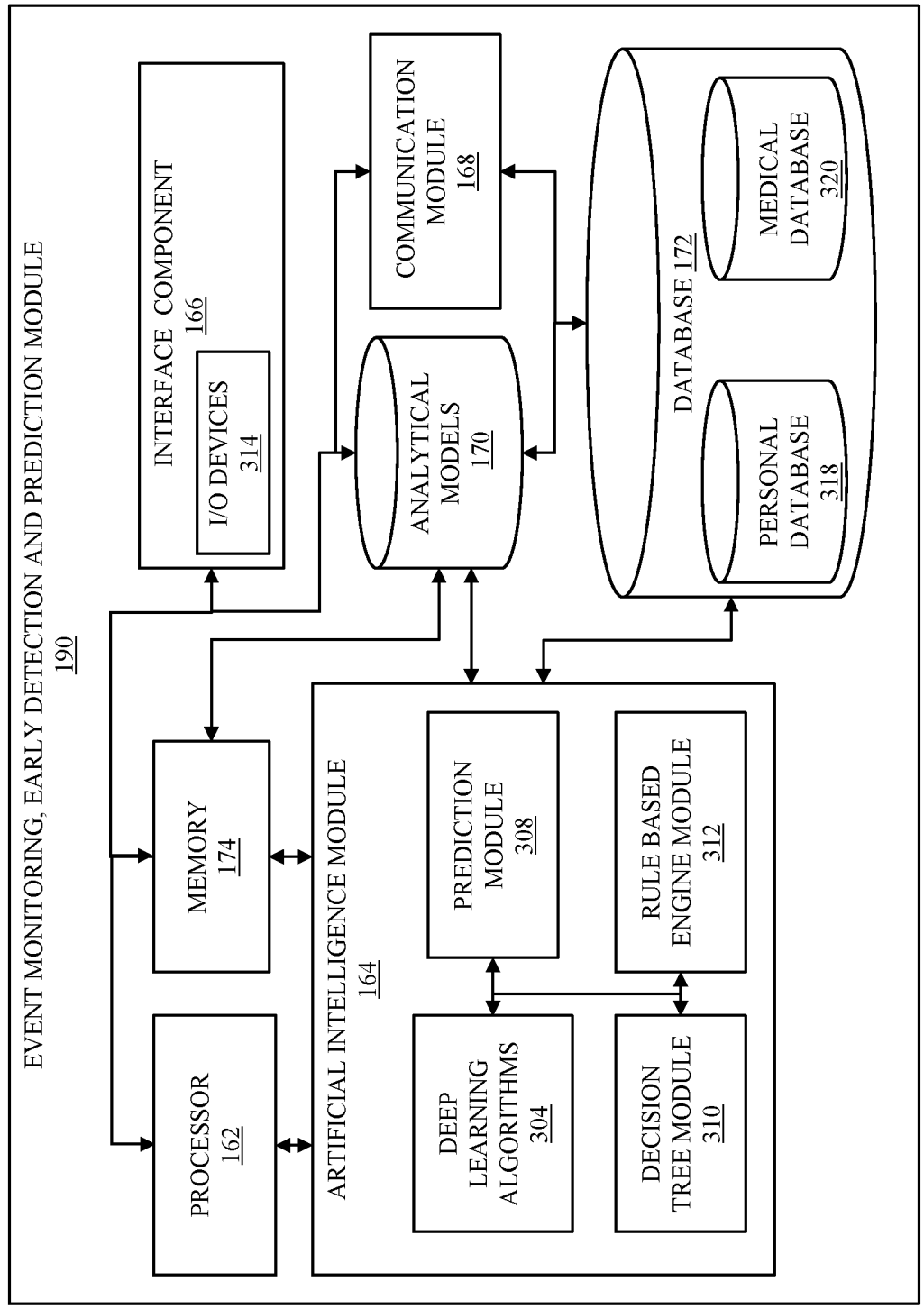
FIG. 3 illustrates different components of an event monitoring, early detection and prediction module in an embodiment of the present invention.

FIG. 3 illustrates different components of an event monitoring, early detection and prediction module in an embodiment of the present invention. The event monitoring, early detection and prediction module 190 includes the processor 162, the memory 174, the artificial intelligence module 164, the interface components 166, the analytical models 170, the communication module 168 and the database 172.

The processor 162 is connected to the memory 174. The memory 174 may store volatile and nonvolatile data that can be accessed by the processor 162. In embodiments, the memory 173 may be a RAM, ROM, flash memory or some other type of memory and may be connected with a cache memory, a primary memory and/or a secondary memory.

The artificial intelligence module 164 includes one or more deep learning algorithms 304, a decision tree module 310, a rule-based engine 312 and a prediction module 308 apart from other modules.

The deep learning algorithms 304 receive the radio frequency and other data for analysis from different data aggregation devices such as the one or more sensors 110, the RFID data from RFID device 140 and the image data from the thermal camera 130. The collected data is a mix of different frequencies from multiple devices, which are filtered and separated using spectral analysis in the signal processing module 120. Finally, the filtered data with different frequencies is passed to the artificial intelligence module 164 for prediction of undesired events for providing forewarning and/or remedial actions to the different stakeholders. In some embodiments, as explained earlier, the filtered data with different frequencies is passed to the artificial intelligence module 164 for prediction of desired events for providing forewarning and/or remedial actions to the different stakeholders.

The one or more deep learning algorithms 304 may implement one or more techniques for data prediction such as but not limited to artificial neural networks, deep neural networks, recurrent neural networks, convolution deep neural networks and other artificial intelligence algorithms and techniques. In some embodiments, the deep learning algorithms may analyze 2-dimensional data for classification of the undesired events by implementing classification algorithms. For example, in one implementation of this embodiment, the 2-dimensional data may be analyzed using multilayer perceptron and/or support vector machines.

The artificial intelligence module 164 also includes the decision tree module 310 for making decisions related to undesired events. The decision tree module 310 has coded instructions with fuzzy logic to decide on which algorithms to be implemented based on the profile of the person 114. In addition, the decision tree module 310 may also decide and select the optimum analytical model 170 based on health data, genetic data, personal data, location of the person and other related parameters. For example, the decision tree module 310 may access the database 172. The database 172 includes a personal database 318 and a medical database 320. The personal database 318 includes personal data comprising name, age, demographics, medical history, treatment, disease, prescription and other types of medical data. Likewise, the medical database 320 may comprise information related to specific disease and treatment protocol(s). The artificial intelligence module 164 selects the analytical model 170 based on one or more parameters selected from personal data and/or personal information, health data and or health information and location information.

The artificial intelligence module 164 includes the rule-based engine module 312. The rule-based engine module 312 is connected with the deep learning algorithms 304 and also connected to the personal database 318 and the medical database 320. The rule-based engine module 312 extracts personal data from the personal database 318 and the medical data related to the current medical state of the person 114 along with the radio frequency data received from the one or more sensors 110 and applied rules to provide information to the decision tree module 310. Based on the received information, the decision tree module 310 selects the right analytical model for prediction of the undesired events for the person 114.

The rule-based engine module 312 is also entrusted with the task of selecting the threshold value based on the profile of the person 114. Each person 114 may have a different profile and based on health information, personal information, genetic information and the location information the threshold for the person 114 is calculated.

In some embodiments, the rule-based engine module 312 is updated by artificial intelligence module 164 based on analyzed data. The decision tree module 310 may internally develop new rules and update the rule-based engine 312 accordingly. The rules are specific to a person and may be based on the additional information that has been received from the database 172.

In embodiments, the rule engine module 312 and the decision tree module 310 may provide information to the prediction module 308. The prediction module 308 may receive inputs from the deep learning algorithms 304, the decision tree module 310, the rule-based engine module 312 and the database 172 comprising personal database 318 and the medical database 320 and accordingly select the analytical model 170. The predicted value is then compared with the threshold value associated with the person 114 to arrive at a decision to trigger an undesired event(s). If the predicted value is greater than the threshold value then the undesired event is triggered else it is bypassed.

In some embodiments, after the undesired event has been predicted, the event monitoring, early detection and prediction module 190 may receive feedback from the caretaker 112 about the success or failure of the prediction. The feedback is used for improving the efficiency of prediction of the undesired events.

Figure 4:
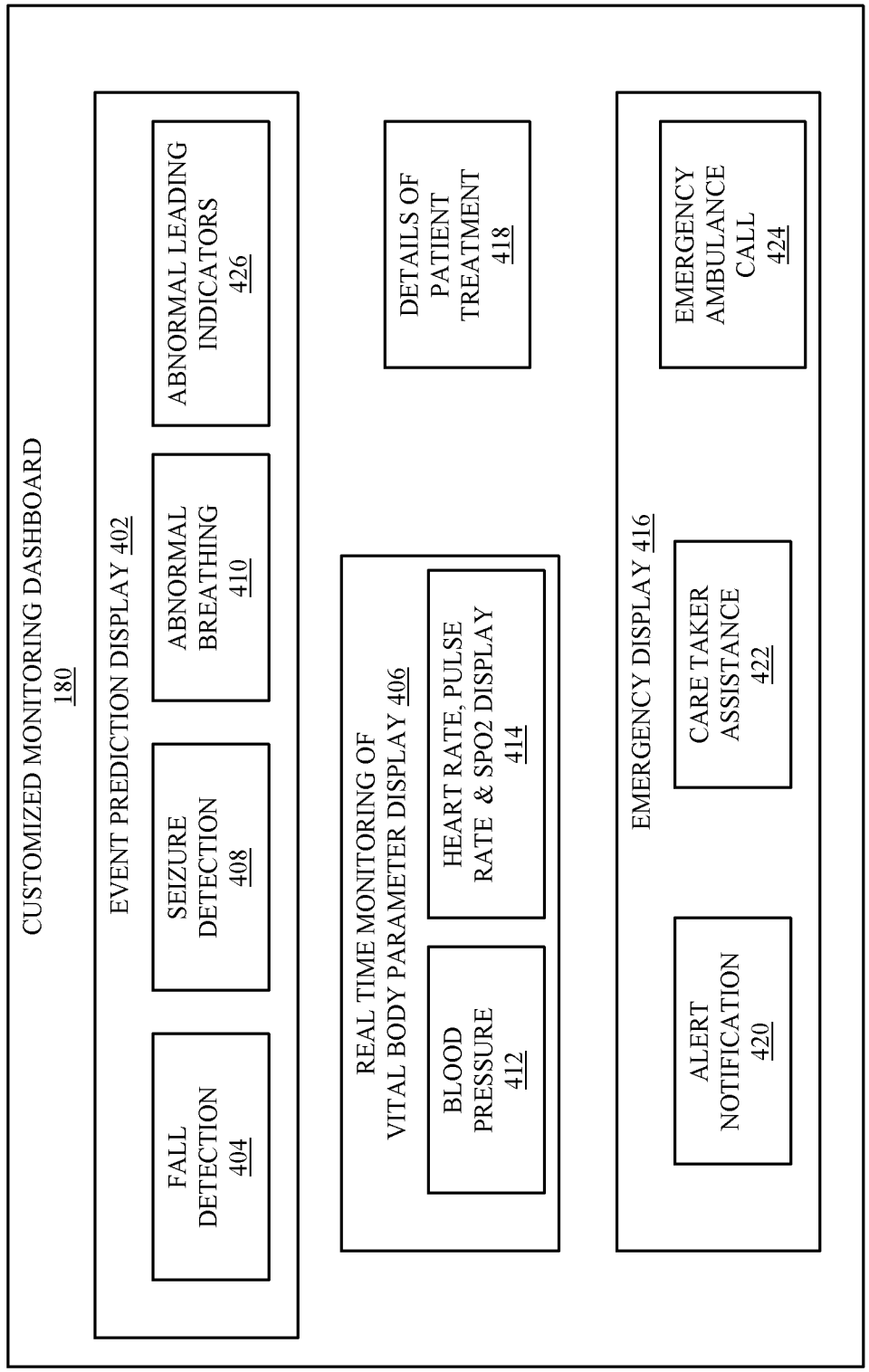
FIG. 4 illustrates a user interface of a monitoring dashboard in an embodiment of the invention.

FIG. 4 illustrates a user interface of a monitoring dashboard in an embodiment of the invention. The monitoring dashboard 180 may include graphics components such an event prediction display 402, a real time monitoring of vital body parameter display 406 and an emergency display 416.

The event prediction display 402 includes a display for fall detection 404, seizure detection 408, abnormal breathing 410 and abnormal leading indicators 426. The event prediction display 402 provides prediction and early detection of the undesired event. The event prediction display 402 may provide prediction, early warning and alert for fall detection in the fall detection display 404. Likewise, event prediction display 402 may provide prediction, early warning and alert for seizure detection in the seizure detection display 408. Similarly, event prediction display 402 may provide prediction, early warning and alert for abnormal breathing in the abnormal breathing display 410. The event prediction display 402 may provide prediction, early warning and alert for abnormal leading indicators 426. For example, abnormal reading indicators may be high blood pressure, increased pulse rate indicating symptoms of some disease. The abnormal leading indicators 426 may be an important indicator for the caretaker 112 or the doctor 118 to arrive at a diagnosis of the disease.

The fall detection display 404 provides an alert and notification in form of a sound or a vibration or a text message to preempt the person 114 to avoid a fall. The fall detection display 404 further alerts the stakeholders regarding the early prediction of a fall of the person 114 and provides instruction for corrective/remedial actions to be taken by the person 114 or the caretaker 112 to avoid a fall.

The seizure detection 408 provides an alert and notification in form of a sound or a vibration or a text message to preempt the person 114 to avoid a seizure. The seizure detection display 408 also alerts the stakeholders regarding early prediction of a seizure and provides instructions for corrective/remedial actions to be taken by the person 114 or the caretaker 112 to avoid a seizure.

In embodiments, the corrective/remedial action may involve taking medication and/or doing relaxation exercise based on early detection of the undesired event.

The abnormal breathing display 410 provides an alert and notification in form of a sound or a vibration or a text message to preempt the person 114 to avoid a shortness of breath. The abnormal breathing display 410 also alerts the stakeholders regarding early prediction of a shortness of breath and provides instructions for corrective/remedial actions to be taken by the person 114 or the caretaker 112 to avoid shortness of breath. For example, one remedial action may be taking medicine as advised by the doctor 118.

The monitoring dashboard 180 further includes the real time monitoring of vital body parameter display 406 and the details of patient treatment display 418. The real time monitoring of vital body parameter display 406 displays the information related to vital body parameters such as but not limited to heath rate, pulse rate, blood pressure, ECG (for a sick patient) and other vital body monitoring parameters. The real time monitoring of vital body parameter display 406 includes a blood pressure display 412 and a heart rate, pulse rate and SpO2 display 414. In addition, the monitoring dashboard 180 also allows the stakeholders to access the details of treatment of the person 114 through the patient treatment display 418. The details of the treatment of the person may be related to past history or current medical treatment of the person 114.

In embodiments, the stakeholders may be the person 114, the caretaker 112, the doctor 118 and other support staff associated with the person 114 such as family members, relatives, and friends.

The real time monitoring of vital body parameter display 406 may provide the stakeholders with the access to the state of health of the person 114 being monitored. For example, the blood pressure display 412 may provide real time blood pressure monitoring of the person 114 to the caretaker 112. In addition, the real time monitoring of vital body parameter display 406 may provide alert and notifications to the person 114 and the caretaker 112 to alert them of critical condition or any predicted undesired event(s). Likewise, the heart rate, pulse rate and SpO2 display 414 may provide real time monitoring of a heart rate of the person 114 and to the caretaker 112. In addition, the contactless monitoring system and early prediction system 160 may provide alert and notifications to the person 114 and the caretaker 112 to alert them of a specific condition that is likely to occur as predicted earlier.

The monitoring dashboard 180 may allow the person 114 and the caretaker 112 to access information through the user interface and interface buttons may be provided to access and browse the details of patient treatment 418. The details of patient treatment 418 may be displayed to provide details such as but not limited to prescription history, diseases both chronic and non-chronic, emergency procedures, and other details related to a person's medical details.

The monitoring dashboard 180 also includes the emergency display 416 for displaying different levels of emergencies and sending notification to different levels of escalation based on the type of emergency. An alert notification 420 addresses emergencies related to undesired events that are not life threatening. For example, the undesired event such as fall or seizure may raise an alert and/or notification for addressing the emergency associated with a person 114. The second level of emergency may relate to events that might require immediate attention of the caretaker 112 to address the undesired early predicted event. A caretaker assistance display 422 raises an alert/notification or an alarm to alert the caretaker 112 to immediately address the early detection of the undesired event. This is categorized as type two emergencies, wherein the caretaker 112 is notified to immediately attend the undesired event. For example, the abnormal breathing may require assistance from the caretaker 112 by providing medicine and/or oxygen.

The highest level of emergency is related to an emergency ambulance call 424. The emergency ambulance call is required when the contactless monitoring system and early prediction system 160 makes an early prediction of an undesired event, which is life threatening. For example, a prediction of a heart stroke as an early detection of the undesired event associated with the person 114. In this scenario, the alerts/notification may initiate a call to the emergency number for calling the doctor 118. In some embodiments, the caretaker 112 calls the emergency number, however in different variations of this implementation, the contactless monitoring system and early prediction system 160 may stream live video and call the emergency number automatically without any human intervention.

In some embodiments, on activation of the emergency ambulance call 424, the event monitoring and early detection system 160 may connect with a hospital to arrange for an ambulance. The contactless monitoring system and early prediction system 160 may open a channel for streaming data providing real time monitoring of vital body parameter display 406 to the hospital. It may be noted that the novel feature of the invention is pre-empting the emergency based on the different parameters such as but not limited to personal attributes, medical history, current treatment, and other parameters to forecast the likelihood of an undersized event or a desired event.

In one embodiment, the contactless monitoring system and early prediction system 160 may be programmed to capture the desired event. The monitoring dashboard 180 can be customized for displaying data related to desired events. The desired event may be related to taking medical treatment or prescription before the onset of the undesired event or asking the person to lie down in case of early prediction of a fall or to take oxygen in case of early prediction of abnormal breathing.

Figure 5:
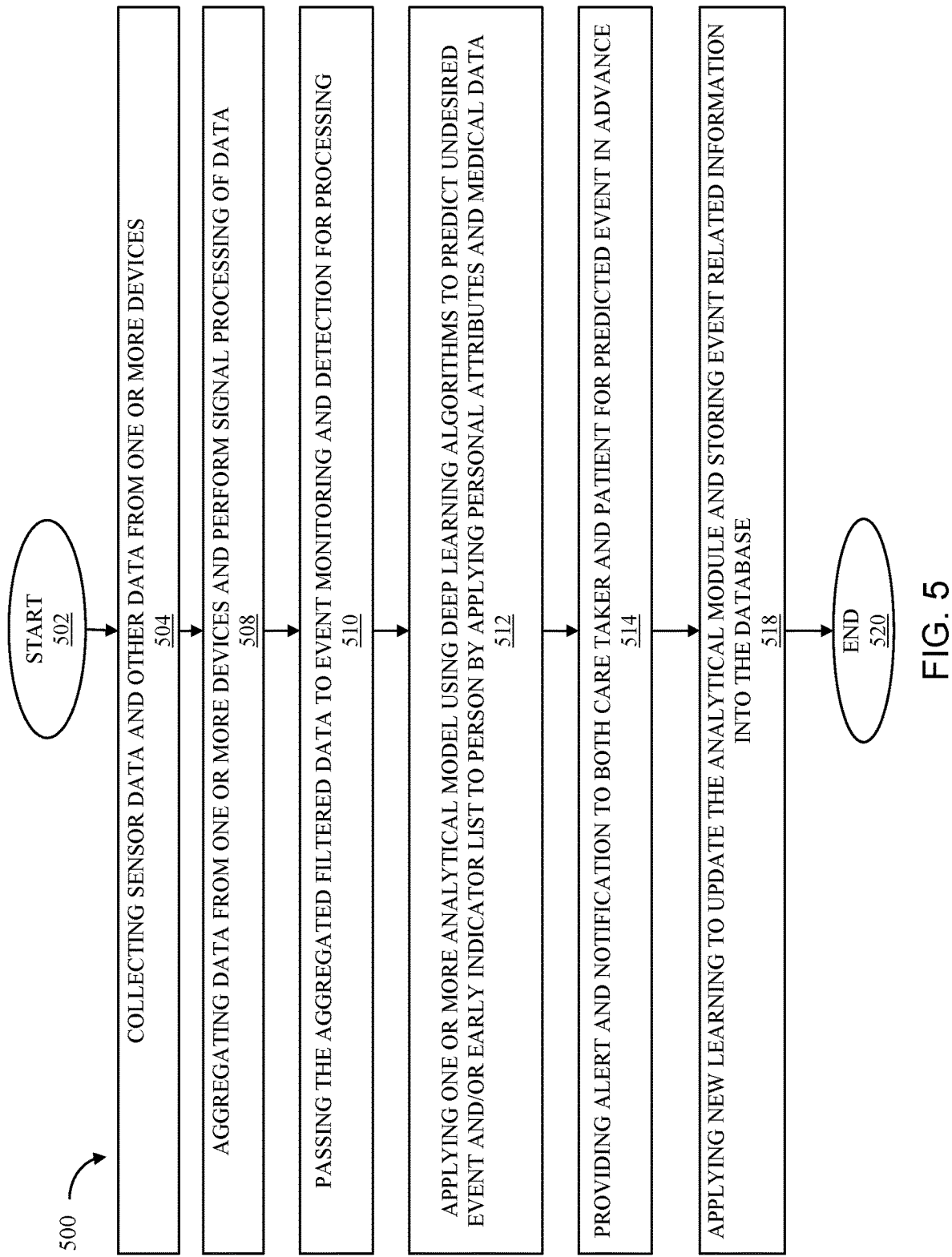
FIG. 5 illustrates a process flow of a contactless event monitoring and detection system in an embodiment of the present invention.

FIG. 5 illustrates a process flow of a contactless event monitoring and detection system in an embodiment of the present invention. The process 500 starts at 502 and immediately moves to 504. At step 504, the process 500 collects data from one or more sensors 110. In addition, the process 500 may collect data from one or more data aggregation devices such as one or more thermal camera 130, one or more RFID devices 140 or other medical devices for contactless monitoring and early detection of the person 114.

In a preferred embodiment, the person 114 is a patient with autism. However, the invention can be practiced to monitor one or more persons 114 in different environments, for example, the contactless monitoring and early detection of an undesired event. The different environments may include airports, public places, malls or parks to monitor one or more persons 114 for suspicious activity by applying deep learning algorithms to predict any undesired act by a passenger or an employed staff member in the airport. The novel feature of the invention allows monitoring of the person even in private areas without conflicting with privacy issues. The one or more sensors may collect data related to different parameters of a person using radio frequency waves and, in this implementation, the thermal or other camera may be removed to avoid conflict with privacy requirements.

At step 508, the collected data from one or more aggregation devices is passed to the signal processing module 120 for filtering, smoothening, and reducing the size of data to transmit data even under low bandwidth. The filtering process 510 may involve eliminating the undesired frequencies and noise, extracting the required signals and reducing the size of signal data for transmission for the early detection, prediction and event monitoring.

At step 512, the process 500 may pass the collected data to event monitoring, early detection and prediction module 190. The received data is processed by a deep learning algorithm for detection of the undesired events associated with person 114. The process of analysis of the collected data includes: forming a decision tree of possible outcomes, applying rules based for prediction, developing an analytical model using the one or more artificial intelligence algorithms and applying analytical model to predict the undesired event associated with the person 114. In addition, the analytical model may also predict the early indicator list and pass it to the caretaker 112 or the person 114. In embodiments, the early indicator list may be the list of symptoms that provide information before the onset of undesired event. For example, the early indication for a heart attack may be chest pain or breathlessness during walking indicating a blockage in the heart.

In different embodiments, the process 500 may apply health related to the person to increase the probability of prediction of the undesired event. In yet another variation, when a person is a patient or a differently abled person, the process 500 may apply medical data of the patient or the differently abled person to increase the probability of prediction. In one embodiment, the probability of prediction is compared with a threshold value. The threshold value is derived based on the profile of the person 114 and varies from person to person. If the predicted value is higher than the threshold value then the undesired event is triggered.

In yet another implementation, the process 500 may apply the demographic data, personal data, location data, and medical data to increase the probability of prediction of the undesired event(s).

At step 514, the process 500 may provide an alert or a notification for predicting the undesired event and preempting/forewarning the person 114 and/or the caretaker 112 of such undesired event. In different embodiments, the undesired event may be related to but not limited to fall detection, seizure detection, and abnormal breathing.

At step 518, the process 500 may apply the learning's from the previous predictions to enhance the performance of the analytical models 170. In some embodiments, the caretaker 112 may provide feedback to the event monitoring, early detection and prediction module 190 related to the success or failure of the previous predictions such as false positive event and/or false negative event to increase the performance of the one or more analytical models 170. The process 500 terminates at step 520.

Figure 6:
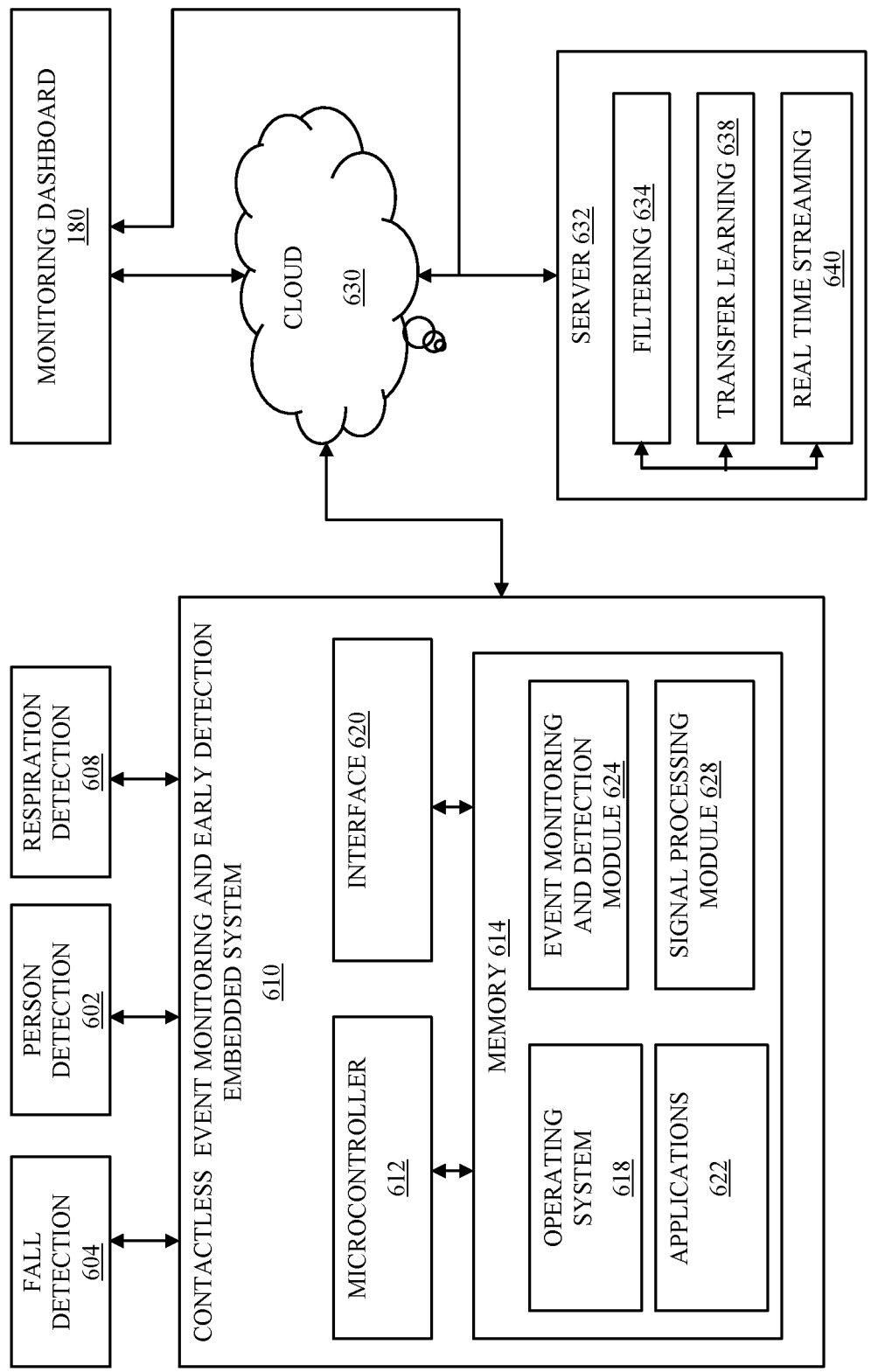
FIG. 6 illustrates a contactless event monitoring and detection system implemented in an embedded system in an embodiment of the present invention.

FIG. 6 illustrates a contactless event monitoring and early detection system implemented as an embedded system in an embodiment of the present invention. The contactless monitoring environment 600 comprises an event monitoring and early detection embedded system 610 with one or more sensors configured to sense fall detection 604, person detection 602, and respiration detection 608, a server 632, a cloud 630, the monitoring dashboard 180 apart from other modules. In some embodiments, the event monitoring and early detection embedded system 610 may include emergency alert/notification for raising an alarm in case of emergency. The event monitoring and early detection embedded system 610 may be a small device that can be attached to the person's body 114 such as a wristband, a headset or a chest enclosure.

The fall detection 604 may be implemented using one or more sensors such as the sensor 110A. For example, the fall detection 604 may be implemented using a motion sensor or other type of fall detection sensor 604. Likewise, the person detection 602 may be implemented with accompanying sensors and circuitry to identify the profile of the person 114. For example, a RFID module may be implemented within the person detection to validate the identity of the person. Similarly, the respiration detection 608 may be implemented with accompanying sensors and circuitry using the respiration detection sensor 608.

The contactless event monitoring and early detection embedded system 610 may include a microcontroller 612, an interface 620, a memory 614 apart from other components. The memory 614 may include either a ROM or a RAM or both. In some embodiments, the memory 614 is a programmable memory, which can be programmed by using a jumper to operate either in read mode to write mode.

The memory 614 may include an operating system 618, one or more applications 622, an event monitoring and detection module 624, and a signal processing module 628. In different embodiments, the operating system may be an Embedded Windows operating system, Embedded Linux operating system or some other type of embedded system. The one or more applications 622 may include programs, which implement wireless protocols to connect the contactless event monitoring and early detection embedded system 610 with the server 632, the cloud 630 and the monitoring dashboard 180 using Bluetooth, Wi-Fi or some other wireless protocols. Alternatively, a wired connection using LAN or WAN is utilized for connection with the server 632, the cloud 630 and the monitoring dashboard 180.

The event monitoring and detection module 624 may include deep learning algorithms 304, the decision tree 310, rule-based module 312, and a prediction module 308. The function of each of these modules has been described in FIG. 3.

In some embodiments, the event monitoring and early detection embedded system 610 may be connected with the medical devices and may capture real time data from the medical device for improving the efficiency of the analytical models 170 and for training itself to accurately predict the early detection of the undesired events.

The contactless event monitoring and early detection embedded system 610 is connected to the cloud 630 and the server 632. The server 632 may include a filtering module 634, a transfer learning module 638, and a real time streaming module 640. In some embodiments, the sensor data is directly provided to the server 632. The filtering module 634 filters the received signal and removes unwanted frequencies before separating different frequencies into frequency bands and then passes it to the transfer learning module 638. The transfer learning module 638 analyzes the filtered data to predict the probability of the undesired event and sends back the processed data to the contactless event monitoring and early detection embedded system 610 for taking corrective/remedial actions.

In an alternate embodiment, the prediction of undesired events happens in the event monitoring and detection module 624, which implements artificial intelligence module and rule-based engine for event monitoring and early detection of an undesired event.

In another implementation, the server 632 processes the health data associated with the person 114 and provides it to the event monitoring and detection module 624 to calculate the threshold value compared with the predicted value for predicting the undesired event.

The event monitoring and early detection embedded system 610 includes the monitoring dashboard 180 for displaying information related to one or more persons 114.

Figure 7:
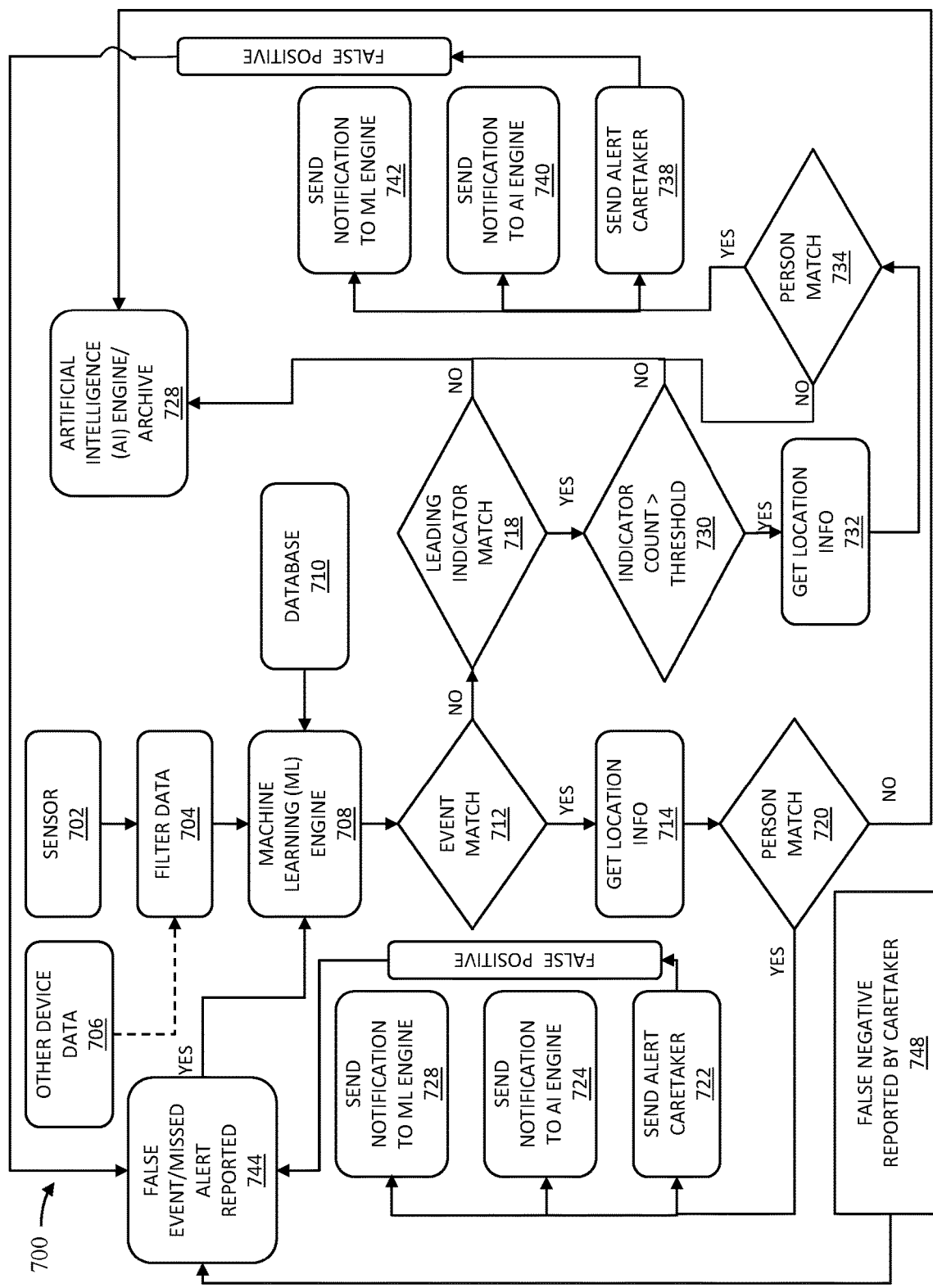
FIG. 7 illustrates a process flow of a contactless event monitoring and detection system in another embodiment of the present invention.

FIG. 7 illustrates a process flow of a contactless event monitoring and early detection system in another embodiment of the present invention. The process 700 starts by collecting data from one or more sensors at step 702. In addition, the process 700 may also collect data from other devices at step 706 such as, thermal camera, RFID devices and other devices. The step 706 is optional, but in other embodiments, the step 706 may be an essential part of the process flow 700.

The data collected from one or more sensors 110 at step 702 and from other devices at step 706 is passed through a filter at step 704. In embodiments, the filter(s) at step 704 may be a digital filter, analog filter or a combination of digital and analog filters. The filter at step 704 filters out the unwanted frequencies and/or noise from the collected data at step 702 and/or at step 706.

The filtered data from step 704 is passed on to a machine learning engine at step 708. The machine learning engine 708 is connected to a database and receives data from the database at step 710. The database includes health data, personal data, genetic data and other types of data. In embodiments, the database 710 may include personal data of a person, medical data of a person, medical history of a person, medical prescription to the person 114 by the doctor 118 and some other type of data. A machine learning engine uses the received data to develop an analytical model using deep learning algorithms for prediction and early detection of the undesired event at step 708.

In one embodiment, the event may be a desired event and the process may be programmed to capture a desired event. For example, reduction in blood pressure to normal blood pressure after inducing medication. Another example of a desired event is directing a person to take medicine after prediction and early detection of a stroke based on early indicators. Likewise, in another example, raising an alarm to the hospital if the blood pressure becomes abnormally high and can't be managed by prescribed medicine.

In another example, the process 700 predicts and detects the possibility of an undesired event based on early indicators in real time. For example, the process 700 may make a prediction of possibility of a seizure based on early indicators such as abnormal breathing prediction. The process 700 may then advise medication or other remedial action to avoid the occurrence of the undesired event.

The prediction of the undesired event associated with the person 114 received from the machine learning engine 708 is evaluated against the list of undesired events to determine if there is a match at step 712. If a match is found, then the process 700 identifies the location information of the person 114 at step 714. Once the location information of the person 114 is obtained at step 714, the process 700 again evaluates to find if the person 114 is from a list of persons. In some embodiments, the person 114 is registered along with his/her profile data. If the person 114 is in the list of persons, which are being monitored then the process 700 sends an alert/notification and to a caretaker 112 at step 722, simultaneously sends a notification to the artificial intelligence engine/module at step 724 and further passes a notification to the machine learning engine/module 728. At step 722 the caregiver 112 may analyze the received alert to determine if a false alert has been created. A false alert may be created when a process 700 creates an alert, which is perceived by the caregiver 112 as unimportant or the alert can be ignored. The caregiver 112 then passed the false alert as false positive (false positive herein refers to an alert that was captured by the system or the process 700 but was designated as unimportant by the caregiver 112) to step 744 as feedback. At step 744, the feedback is analyzed and the learning from the feedback may be passed to the machine learning engine/module for refinement of analytical models and/or to assimilate new learning's.

Otherwise, if no match is found at step 720 within the list of persons for the undesired event associated with the person 114 at step 712 then the process 700 passes the data onto the artificial intelligence engine/archive 728. However, if a match is found for the location as determined in step 714 and the event determined at step 712, In some embodiments, the feedback from step 744 related to false positives may be provided to the artificial intelligence engine at step 728.

Moving back to step 712, when no match is found for the undesired event associated with a person 114, then the process 700 at step 718 evaluates to match the leading indicator with the undesired event.

In embodiments, the leading indicators may include but are not limited to irregular heartbeat, irregular pulse rate, abnormal blood pressure, irregular RPM (Respiration per minute), change in normal movement—freeze or rapid movement of a body part or some other type of abnormal medical condition. For each of the leading indicators, there is a normal range of values in medical diagnostic and the process 700 takes the upper value and lower value of the normal range of leading indicators as the threshold value. Any value that is greater than the upper threshold value is considered for further evaluation and processing. For example, the normal breathing rate of a healthy person is between 12-16 breaths per minute. In this example, the threshold values for the leading indicator that is breaths per minute may be set to 15 breaths per minute. In some embodiments, the breaths per minute may be determined based on the past medical data of the person and the process 700 may accordingly set the value of the breath rate for the person 114.

If no match is found for the leading indicator at step 718, then the step 718 forwards the undesired event information to the artificial intelligence engine/archive 728. The artificial intelligence engine/archive 728 updates deep learning algorithms for new learning and archives the data to build or improve one or more analytical models.

Moving further if a match for a leading indicator is found at step 718, then the process 700 at step 730 performs additional evaluation for assessing if the leading indicator is above or below, that is, greater than or less than a threshold value (lower value and upper value of the normal range of leading indicators). In some embodiments, there may be only an upper value for the leading indicator and the lower value may be insignificant. In this case, the process 700 may evaluate only the upper value with the threshold value)

If the leading indicator count is greater than the upper threshold value or less than the lower threshold value then at step 730 then the process 700 gets the location information of the person at step 732. Otherwise, the process 700 then the process 700 passes the undesired event data onto the artificial intelligence engine/archive at step 728.

Once the location information of the person has been obtained, the process 700 at step 732 evaluates to find a match of the person 114 from the list of persons currently being monitored. If the person 114 fails to match with the list of persons under observation, then process 700 passes the evaluated data to the artificial intelligence engine/archive at step 728. However, if a match of the person 114 is found with the list of persons currently being monitored then process 700 sends an alert to the caretaker 112 at step 738. At step 738, the caretaker 112 may analyze the received alert to determine if it is a false alert. A false alert may be created when a process 700 creates an alert, which is perceived by the caretaker 114 as unimportant or the alert can be ignored. The caretaker 112 then passed the false alert as false positive to step 744 as feedback. The alert/notification of the undesired event associated with person 114 at step 734 is also passed to the artificial intelligence engine/module at step 740 and the machine learning engine module at step 742. At step 744, the feedback is analyzed and the learning from the feedback may be passed to the machine learning engine for refinement of analytical models and/or assimilate new learning.

In some embodiments, the feedback from the step 744 related to false positives may be provided to the artificial intelligence engine at step 738.

The process 700 has an additional step 748 to capture a false negative. A false negative occurs when no alert has been captured by the process 700 but there was an occurrence of an undesired event. The process 700 may not raise an alert even when an event has occurred, for example, a desired or undesired event. The alert event is referred to as false negative. A false negative can only be observed by the person 114 being monitored or the caretaker 112 and reported to the event monitoring and early detection module 190. At step 748, the person 114 being monitored or the caretaker 112 may report a false negative alert to step 744 as a feedback. At step 744, the false alert/missed alert may be analyzed and passed to the machine learning engine at step 708 for updating the analytical models or assimilating the new learning from the false negative event for better prediction.

The features, structures, or characteristics of the present invention described throughout this specification may be combined in any suitable manner in one or more embodiments. The different embodiments and implementations shown herein and the illustrated example and for the purposes of providing what is believed to be the most useful and readily understood description of the principles and conceptual aspects of the present invention in a non-limiting manner.

I claim:

1. A computer implemented contactless event monitoring and early detection method for real time monitoring of at least one person to predict an undesired event, the contactless event monitoring and early detection method comprising:
    collecting in parallel contactless data of the at least one person located in one or more rooms using a one or more data aggregation devices connected to an event monitoring, early detection and prediction system, wherein the one or more aggregation devices comprising at least one or more sensors, a one or more RFID devices and a one or more cameras;
    filtering and analyzing the collected data for at least one person in a signal processing module associated with the event monitoring, early detection and prediction system having a signal processor, wherein the signal processing module comprises a signal filter and a signal analyzer;
    processing the filtered data for each person in parallel in an event monitoring, early detection and prediction module comprising:
        an artificial intelligence module implementing artificial intelligence algorithms in a parallel processing environment to predict the probability of the occurrence of the undesired event for at least one person based on health data stored in a database, wherein the database stores health data, dietary data and behavioral data related to each person and includes early indicators associated with the person, and wherein each early indicator has an upper value and a lower value;
        determining a threshold value for each person, wherein the threshold value is at least based on the upper value of at least one parameter of the health data of the person;
    selecting an analytical model to be applied for prediction of the undesired event, wherein the probability of occurrence of the undesired event is associated with a threshold value;
        predicting an undesired event based on a predicted value for the person;
    comparing the predicted value with the threshold value of the person and if the predicted value is greater than the threshold value then determining the occurrence of undesired event;
    determining the location of the person based on data processed from one or more aggregation devices and matching the profile information of the person, and
    preempting the person associated with the undesired event by sending an alert to the person and/or a caretaker for remedial action.

2. The computer implemented contactless event monitoring and early detection method of claim 1, wherein the undesired event is at least one of a fall, a seizure or an abnormal breathing of the person.

3. The computer implemented contactless event monitoring and early detection method of claim 1, wherein the remedial action involves taking a preventive medicine.

4. The computer implemented contactless event monitoring and early detection method of claim 1, wherein the health data includes at least one of a personal data, a disease history, a medication data and genetic data of the person.

5. The computer implemented contactless event monitoring and early detection method of claim 1, wherein the threshold value is updated based on learnings associated with on health data of the person.

6. The computer implemented contactless event monitoring and early detection method of claim 1, wherein the threshold value is automatically set by the artificial intelligence algorithms based on the training data set.

7. The computer implemented contactless event monitoring and early detection method of claim 1, wherein the one or more RFID devices and a the one or more thermal cameras provide the location of the person.

8. The computer implemented contactless event monitoring and early detection method of claim 1, wherein the analytical models are updated based on learnings associated with the health data of the person.

9. A contactless event monitoring and early detection system for real time monitoring of one or more persons implementing parallel processing to predict an undesired event associated with one or more persons, the contactless event monitoring and early detection system comprising:
    a one or more data aggregation devices for collecting real time contactless data of one or more persons in parallel, the one or more data aggregation devices comprising at least one or more sensors, a one or more RFID devices and a one or more cameras;
    a signal processing module comprising:
        a signal filter for filtering and removing the unwanted frequencies from the collected data for each person;
        a spectral analyzer for analyzing the signal spectrum of collected data from one or more aggregation devices for each person;
        a signal smoother and a signal amplifier for amplifying the collected data;
        a database for storing the health data, dietary data and behavioral data associated with each person, wherein the health data comprises early indicators associated with each person and includes a upper value and a lower value for each of the collected parameters from one or more aggregation devices;
    an event monitoring, early detection and prediction module comprising:
        an artificial intelligence module comprising deep learning algorithms and a rule-based engine, the deep learning algorithms and the ruled based engine are trained using training data set stored in a database for building an analytical model to predict the undesired event for each person;

selecting an analytical model to be applied for prediction of the undesired event based on the health data of the person;

a prediction module for calculating a threshold value based on the upper value of at least one of the parameters associated with the health data of the person and implementing at least one of the analytical models to determine predicted value in real time based collected data from one or more aggregation devices associated with the person;

comparing the predicted value with the threshold value of the person to predict the occurrence of the undesired event and if the predicted value is greater than the threshold value then predicting the undesired event associated with the person;

determining the location of the person based on data processed from one or more aggregation devices and matching the profile information of the person to identify the identity of the person, and sending an alert to forewarn the person and a caretaker by sending a notification or alert to take a remedial action.

10. The contactless event monitoring and early detection system of claim 9, wherein the undesired event is at least one of a fall, a seizure or an abnormal breathing of the person.

11. The contactless event monitoring and early detection system of claim 9, wherein the remedial action involves taking a preventive medicine.

12. The contactless event monitoring and early detection system of claim 9, wherein the health data includes at least one of a personal data, medication data, disease history, dietary and genetic data of the person.

13. The contactless event monitoring and early detection system of claim 9, wherein the threshold value is based on the learning of the deep learning algorithms early indicator associated with the person.

14. The contactless event monitoring and early detection system of claim 9, wherein the threshold value is automatically set by the artificial intelligence algorithms based on the training data set.

15. The contactless event monitoring and early detection system of claim 9, wherein the one or more RFID devices and the one or more thermal cameras provide the location of the person.

16. The contactless event monitoring and early detection system of claim 9, wherein the analytical models are developed using one or more training data set.

17. A computer implemented method of correcting an error in prediction of an undesired event associated with at least one person in a parallel processing environment during real time monitoring of one or more persons, the contactless event monitoring and early detection method comprising step of:

collecting contactless data for one or more persons simultaneously from a one or more data aggregation devices including at least a one or more sensors, a one or more RFID, a one or more camera;

filtering the collected data in parallel for each person in a signal processing module having a signal processor comprising a signal filter and a signal analyzer, wherein the signal filter removes unwanted frequencies and the signal analyzer analyzes the collected data;

passing the collected data to an event monitoring, early detection, and prediction module for each person comprising:

an artificial intelligence module implementing artificial intelligence algorithms, which are trained using a training data set to predict the probability of the occurrence of the undesired event for each person by determining a predicted value in real time;

receiving a health data, dietary data and behavioral data of the person to determine a threshold value, wherein the health data includes early indicators and each early indicator has a lower value and a upper value for each parameter associated with each person;

selecting an analytical model based on the health data of the person to be applied for prediction of the undesired event, wherein the probability of occurrence of the undesired event is determined by a predicted value and wherein the threshold value is associated of at least one of the early indicators;

comparing the predicted value with threshold value of the person and wherein the threshold value is based on the upper value of at least one of early indicators collected by one or more aggregation devices and associated with each person;

raising an alert for occurrence of the undesired event and if the predicted value is greater than the threshold value then predicting the undesired event associated with the person;

receiving an input from the person or a caretaker that the prediction of the undesired event was a false positive alert or a false negative alert;

re-training the artificial intelligence algorithms to correct the false prediction of the undesired event for that person to updated at least one analytical model, and storing the updated analytical model for that person in the analytical models and using the updated analytical model for predicting and undesired events.

18. The computer implemented method of correcting the error in the contactless event monitoring and early detection method of claim 17, wherein the undesired event is false positive.

19. The computer implemented method of correcting the error in the contactless event monitoring and early detection method of claim 17, wherein the undesired event is false negative.

20. The computer implemented method of correcting the error in the contactless event monitoring and early detection method of claim 17, wherein the early indicators are associated with the undesired event.

* * * * *